United States Patent [19]

Wehinger et al.

[11] Patent Number: 4,849,433
[45] Date of Patent: Jul. 18, 1989

[54] THE COMPOUND, (⇌)1,4-DIHYDRO-2,6-DIMETHYL-4-(2'-NITROPHENYL)-PYRIDINE-3,5-DICARBOXYLIC ACID, METHYL ISOBUTYL ESTER, COMPOSITIONS CONTAINING SAME AND A METHOD FOR EFFECTING CORONARY DILATION

[75] Inventors: Egbert Wehinger, Velbert; Horst Meyer; Friedrich Bossert, both of Wuppertal; Wulf Vater, Leverkusen, all of Fed. Rep. of Germany; Robertson Towart, Slough, England; Kurt Stoepel; Stanislav Kazda, both of Wuppertal, Fed. Rep. of Germany

[73] Assignee: Bayer Aktiengesellschaft, Leverkusen, Fed. Rep. of Germany

[21] Appl. No.: 12,515

[22] Filed: Feb. 9, 1987

Related U.S. Application Data

[63] Continuation of Ser. No. 718,916, Apr. 2, 1985, abandoned, which is a continuation-in-part of Ser. No. 429,832, Sep. 30, 1982, Pat. No. 4,510,310, which is a continuation of Ser. No. 181,453, Aug. 25, 1980, abandoned.

[30] Foreign Application Priority Data

Sep. 1, 1979 [DE] Fed. Rep. of Germany ....... 2935451

[51] Int. Cl.$^4$ .................. C07D 21/90; A61K 31/44
[52] U.S. Cl. .................. 514/356; 546/257; 546/270; 546/321
[58] Field of Search .................. 546/321; 514/356

[56] References Cited

U.S. PATENT DOCUMENTS 3,799,934  3/1974  Meyer et al. ............... 546/257
3,985,758  10/1976  Murakami et al. ......... 546/321
4,044,141  8/1977  Bossert et al. ............. 514/356

OTHER PUBLICATIONS

Jacques et al., Enantiomers, Racemates and Resolutions, pp. 251–261, Wiley–Interscience Pub., QD 481 J.3(1981).

Primary Examiner—Alan L. Rotman
Attorney, Agent, or Firm—Sprung, Horn, Kramer & Woods

[57] ABSTRACT

The invention relates to optically active 1,4-dihydropyridine compounds of Formulas Ia and Ib as defined hereinabove which are effective for influencing circulation. Also included in the invention are compositions containing said optically active compounds and methods for the use of said compounds and compositions.

9 Claims, No Drawings

THE COMPOUND, (⇌)1,4-DIHYDRO-2,6-DIMETHYL-4-(2'-NITROPHENYL)-PYRIDINE-3,5-DICARBOXYLIC ACID, METHYL ISOBUTYL ESTER, COMPOSITIONS CONTAINING SAME AND A METHOD FOR EFFECTING CORONARY DILATION

This is a continuation, of application Ser. No. 718,916, filed Apr. 2, 1985 (now abandoned), which is a continuation in part of Ser. No. 429,732 filed Sept. 30, 1982 now U.S. Pat. No. 4,510,310 which in turn is a continuation of Ser. No. 181,453 filed Aug. 25, 1980 (now abandoned).

The present invention relates to new optically active 1,4-dihydropyridine compounds, to processes for their production and to their use as agents which influence the circulation.

It has already been disclosed that certain 1,4-dihydropyridine derivatives have interesting pharmacological properties and can be used, in particular, as agents which influence the circulation (see F. Bossert, W. Vater, Naturwissenschaften 58, 578 (1971) and DT-OS 2,117,571 (German Published Specification corresponding to U.S. Pat. No. 3,799,934). All the pharmacologically active 1,4-dihydropyridine derivatives known hitherto are either achiral compounds or racemic forms of chiral compounds.

It is furthermore known that attempts have already been made to resolve racemic forms of chiral, variously substituted 1,4-dihydropyridine derivatives, but the preparation and isolation of pure antipodes has not previously been successful (see J. A. Berson and E. Brown, J. Amer. chem. Soc. 77, 450 (1955). The optically active antipodes of chiral 1,4-dihydropyridine derivatives, like those of the preparation processes of the present invention below, are thus new and represent an enrichment of the art.

According to the present there are provided compounds which are the antipodes of chiral 1,4-dihydropyridinecarboxylic acid esters with different, achiral substituents, of the formula

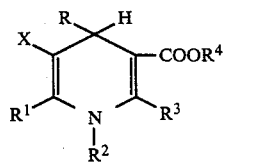

(Ia)

or a salt(particularly (1) a pharmaceutically acceptable acid addition salt or (2) an alkali or-alkaline earth metal salt of those compounds in which $R_4$ is hydrogen)-thereof, or are 1,4-dihydropyridinecarboxylic acid esters of the formula

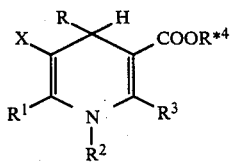

(Ib)

in which

R represents an aryl radical or a heterocyclic radical selected from thienyl, furyl, pyrryl, pyrazolyl, imidazolyl, oxazolyl, isoxazolyl, thiazolyl, pyridyl, pyridazinyl, pyrimidyl, pyrazinyl, quinolyl, isoquinolyl, indolyl, benzimidazolyl, quinazolyl and quinoxalyl, the aryl radical and the heterocyclic radicals mentioned optionally containing 1,2 or 3 identical or different substituents selected from phenyl, alkyl, alkenyl, alkinyl, alkoxy, alkylene, dioxyalkylene, halogen, trifluoromethyl, trifluoromethoxy, alkylamino, nitro, cyano, azido, carboxamido, sulphonamido and $SO_m$-alkyl (in which m is 0 or 2), $R^1$ and $R^3$ are identical or different and in each case denote a hydrogen atom, an achiral straight-chain or branched alkyl radical, an aryl radical, or an aralkyl radical, $R^2$ denotes a hydrogen atom, an achiral, straight-chain or branched alkyl radical which is optionally interrupted by an oxygen atom to form, e.g. an oxa-alkylene chain, an aryl radical or an aralkyl radical, X (a) denotes a nitrile, i.e. cyano radical, or (b) denotes a group of the formula $—COR^5$, in which $R^5$ denotes an achiral, optionally substituted alkyl, aryl or aralkyl radical, or (c) denotes a group of the formula $—COOR^6$, in which $R^6$ denotes an achiral, straight-chain, branched or cyclic, saturated or unsaturated hydrocarbon radical which is optionally interrupted in the chain by oxygen, sulphur (to form, e.g. an oxa- or thia-alkylene chain) or the $—SO_2—$ group and which is optionally substituted by halogen, pyridyl, phenyl, phenoxy, phenylthio or phenylsulphonyl, it being possible for the phenyl groups in turn to be substituted by halogen, cyano, dialkylamino, alkoxy, alkyl, trifluoromethyl or nitro, or it being possible for the hydrocarbon radical to be substituted by an amino group, this amino group being substituted by two identical or different substituents selected from alkyl, alkoxyalkyl, aryl and aralkyl, or the amino group being substituted in a manner such that 2 substituents, together with the nitrogen atom, form a 5-membered to 7-membered ring, which optionally contains, as a further hetero-atom, oxygen or sulphur, or a N-alkyl grouping, or (d) denotes a group of the general formula $SO_2$-$R^7$, in which $R^7$ an archiral straight-chain, branched or cyclic, saturated or unsaturated aliphatic hydrocarbon radical which is optionally interrupted in the chain by an oxygen (to form an oxa-alkylene chain, for example, or an oxa-alkylene or an oxa-alkenylene or oxa/alkadienyl ring and which is optionally substituted by an aryl radical selected from phenyl, phenoxy, phenylthio. phenylsulphonyl and pyridyl or by an amino group, it being possible for the said aryl radicals in turn to be optionally substituted by halogen, cyano, dialkylamino, alkoxy, alkyl, trifluoromethyl or nitro and the amino group being optionally substituted by two identical or different substituents selected from alkyl, alkoxyalkyl, aryl and aralkyl, or 2 of these substituents, with the nitrogen atom, optionally forming a 5-membered to 7-membered ring, which optionally contains, as a further hetero-atom, oxygen or sulphur, or the N-alkyl grouping, or in which $R^7$ denotes an aryl radical which optionally contains 1, 2 or 3 identical or different substituents selected from alkyl, alkoxy, halogen, cyano, trifluoromethyl, trifluoromethoxy, dialkylamino and nitro, and $R^4$ independently of $R^6$ has any of those meanings given for $R^6$, the two substituents in the 3-position and 5-position always being different from one another, or $*R^4$ represents a chiral hydrocarbon radical having a single configuration which optionally contains 1, 2 or 3 identical or different electron-attracting radicals selected from nitrile, COO-alkyl, COO-aryl, COO-aralkyl, amino and hydroxyl, the amino and hydroxyl groups optionally being alkylated, aralkylated, acylated, acetalised or silylated.

As used herein and unless otherwise indicated, "aryl" preferably means mono- or bi-cyclic carbocyclic aryl; "alkyl" preferably contains 1 to 8 especially 1 to 3 or 4 carbon atoms; "alkenyl" and "alkinyl" preferably contain 2 to 8 especially 2,3 or 4 carbon atoms; "alkylene" preferably contains 2 to 4 carbon atoms; "dioxyalkylene" preferably contains 2 to 4 carbon atoms; "halogen" is preferably chloro or fluoro or bromo' "alkylamino or" dialkylamino preferably contains 1 to 8, especially 1 to 3 or 4 carbon atoms in each alkyl group; "aralky" preferably is mono- or bi-cyclic carbocyclic aryl in the aryl portion and 1 to 4, especially 1 or 2 carbon atoms in the alkyl portion; a "straight-chain or branched alkyl radical which is interrupted by an oxygen or sulfur atom" is preferably oxa- or thina-alkylene or dioxaor dithia-alkylene; "cyclic hydrocarbon" is preferably cycloalkyl, cycloalkenyl or cycloalkadienyl heaving 3 to 8, especially 5 to 6 ring carbon atoms; and "alkoxyalkyl" preferably contains 1 to 3 or 4 carbon atoms in each alkyl portion.

The compounds of the formula (Ib) according to the invention on the one hand have the same advantageous pharmacological properties as the compounds of the general formula (Ia), and moreover serve as valuable intermediate products, via which the compounds of the formula (Ia) can be obtained in a simple manner by transesterification of the chiral substituent *R$^4$ (see process variant (c) below).

According to the present invention there is further provided a process for the production of a compound of the present invention (an antipode of formula (Ia), or a salt thereof, or a compound of formula (Ib)) in which (a) the corresponding racemates of the formula

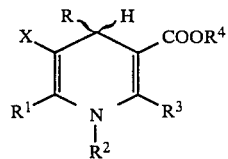

(II)

in which the substituents R, R$^1$, R$^2$, R$^3$, R$^4$ and X have the meaning indicated above are allowed to interact with a chiral substance, the diastereomeric relationships between the two antipodes of the dihydropyridine and the chiral substance being used to separate the antipodes, or (b) the optically inactive racemic forms of a 1,4-dihydropyridinecarboxylic acid of the generalformula

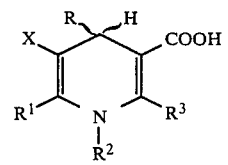

(III)

in which

R, R$^1$, R$^2$, R$^3$ and X have the meanings indicated above, are reacted with an optically active base to give the corresponding diastereomeric salts and, after separation of the antipodes, the respective salts are converted into the optically active 1,4-dihydropyridinecarboxylic acids of the formula

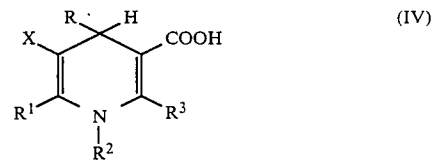

(IV)

in which

R, R$^1$, R$^2$, R$^3$ and X have the meanings indicated above and the optically active acids are then esterified with an alcohol derivative of the general formula HOR$^4$ (V) or *HOR$^4$ (Va) in which R$^4$ and *R$^4$ have the meanings indicated abvve, to give a compound of the present invention, or (c) a 1,4-dihydropyridine with an optically active alcohol component in the ester radical —*R$^8$, of the formula formula

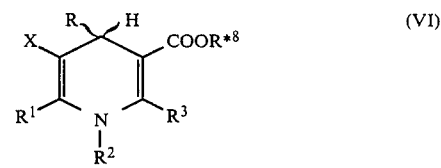

(VI)

in which

R, R$^1$, R$^2$, R$^3$ and X have the meanings indicate above and *R$^8$ has meaning given for *R$^4$ or denotes a sugar residue which is optionally peralkylated, acetylated or acetalised, is prepared by one of the processes for the synthesis of 1,4-dihydropyridines, using appropriate optically active starting materials, and the diastereomers obtained by this prccess are separated by virtue of the two possible different configurations on the C$_4$ atom of the dihydropyridine ring, the resulting 1,4-dihydropyridine with the chiral ester group, of the formula

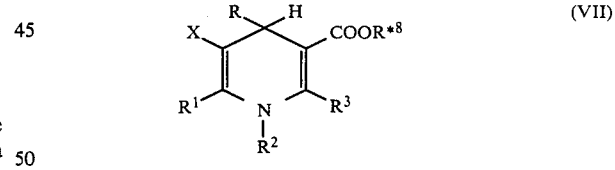

(VII)

in which

R, R$^1$, R$^2$, R$^3$, *R$^8$ and X have the meaning indicated above, being trans-esterified by replacing the chiral ester radicat *R$^8$ by an achiral ester radical R$^4$, to give a compound of the formula (Ia), or by another chiral ester radical *R$^4$, to give a compound of the formula (Ib), or the derivative of formula (VII) of single configuration being hydrolysed to give a compound of formula (IV) as defined in reaction variant (b), which is then esterified with an alcohol derivative of formula (V) or (Va) as described in reaction variant (b).

The compounds of the present invention, the optically active 1,4-dihydropyridines of the formula (Ia), and their salts, and of formula (Ib)) have valuable pharmacological properties. On the basis of their circulation-influencing action, they can be used as antihypertensive agents, as peripheral and cerebral vasodilators and as coronary therapeutic agents. It has been found that the pharmacological action of the dihydropyridines according to the invention depends on the configuration, and that one of the antipodes always has a significantly better action than the corresponding racemate. Moreover, it was completely unexpected that the pharmacological action is not influenced by the different configurations in the chiral ester radical, but solely by the configuration of the carbon atom in the 4-position of the dihydropyridine ring. This unexpected finding means that the expert is in a position to use the valuable properties, which are already known, of dihydropyridines more specifically, to prepare new galenical formulations with a lower content of active compound and to reduce undesired pharmacological side effects. The new optically active 1,4-dihydropyridines according to the invention thus represent an enrichment of pharmacy.

Particularly preferred compounds of the present invention are those in which

R denotes a phenyl, biphenyl, naphthyl, thienyl, furyl, pyrryl, pyrazolyl, imidazolyl, oxazolyl, isoxazolyl, thiazolyl, pyridyl, pyridazinyl, pyrimidyl, pyrazinyl, quinolyl, isoquinolyl, indolyl, benzimidazolyl, quinazolyl, or quinoxalyl, radical, the rings thereof being substituted one or two identical or different substituents selected from alkyl, cycloalkyl, alkenyl, alkinyl and alkoxy with in each case up to 7 carbon atoms, trimethylene, tetramethylene, pentamethylene, dioxymethylene, halogen, trifluoromethyl, trifluoromethoxy, nitro, cyano, azido, mono- and di-alkylamino with in each case 1 to 4 carbon atoms in the alkyl radical, carboxamido, sulphonamido and the radical $SO_m$-alkyl, in which m is 0 or 2 and "alkyl" contains 1 to 4 carbon atoms, and $R^1$ and $R^3$ are in each case identical or different and denote a hydrogen atom or an achiral straight-chain or branched alkyl radical with 1 to 4 carbon atoms, a phenyl radical or a benzyl radical, $R^2$ denotes a hydrogen atom or an achiral strainght-chain or branched alkyl radical which has 1 to 8 carbon atoms and is optionally interrupted in the alkyl chain by an oxygen, or a phenyl or benzyl radical, X (a) denotges a nitrile radical or (b) denotes a group of the general formula —$COR^5$ in which $R^5$ denotes an achiral straight-chain or branched alkyl radical with 1 to 4 carbon atoms, phenyl or benzyl, or (c) denotes a group of the general formula —$COOR^6$, in which $R^6$ denotes an achiral straight-chain, branched or cyclic, saturated or unsaturated hydrocarbon radical which has up to 8 carbon atoms, is optionally interrupted once in the alkyl chain by oxygen, sulphur or the —$SO_2$— group and is also substituted by fluorine, chlorine, bromine or trifluoromethyl or by phenyl, phenoxy, phenylthio or phenylsulphonyl, the phenyl radicals in turn being optionally mono-substituted or disubstituted by fluorine, chlorine, bromine, cyano, nitro or trifluoromethyl or by alkyl, alkoxy or dialkylamino with in each case 1 to 4 carbon atoms in the alkyl and alkoxy radicals, or the hydrocarbon radical is optionally substituted by α-, β- or γ-pyridyl or by an amino group, this amino group optionally carrying two identical or different substituents selected from alkyl with 1 to 4 carbon atons, alkoxyalkyl with up to 6 carbon atoms, phenyl, benzyl and phenethyl, or the nitrogen of this amino group, with the substituents, forming a 5-membered to 7-membered ring, which optionally contains, as a further hetero-atom, an oxygen or sulphur atom, or an N-alkyl group with 1 to 4 carbon atoms in the alkyl radical, or (d) denotes a group of the general formula —$SO_2$—$R^7$, in which $R^7$ denotes an achiral straight-chain, branched or cyclic, saturated or unsaturated aliphatic hydrocarbon radical which has up to 6 carbon atoms, is optionally interrupted in the chain by an oxygen atom and it optionally substituted by phenyl, phenoxy, phenylthio or phenylsulphonyl, the phenyl radicals mentioned being in turn likewise monosubstituted or disubstituted by fluorine, chlorine, bromine, cyano, nitro or trifluoromethyl or by alkyl, alkoxy or dialkylamino with in each case 1 to 4 carbon atoms in the alkyl or alkoxy radicals, or the hydrocarbon radical is substituted by α-, β-or γ-pyridyl or by an amino group, this amino group carrying two identical or different substituents selected from alkyl and alkoxyalkyl with in each case up to 4 carbon atoms, phenyl, benzyl and phenethyl, or the substituents of this amino group, with the nitrogen atom, forming a 5-membered to 7-membered ring, which optionally contains, as a further heteroatom, an oxygen or sulphur atom, or a N-alkyl grouping, that alkyl group containing 1 to 3 carbon atoms, or in which $R^7$ denotes a phenyl radical which is optionally substituted by 1, 2 or 3 identical or different substituents selected from nitro, cyano, trifluoromethyl, trifuloromethoxy, fluorine, chlorine, bromine, alkyl, alkoxy and dialkylamino, the alkyl and alkoxy radicals mentioned containing, in each case, 1 to 4 carbon atoms, and $R^4$ independently of $R^6$, has any of the meanings given for $R^6$, the two substituents in the 3-position and 5-position always being different from one another, or *$R^4$ denotes a chiral, aliphatic hydrocarbon radical having a single configuration and up to 8 carbon atoms and optionally contains 1, 2 or 3 identical or different electron-attracting radicals selected from nitrile, COO-alkyl with 1 to 4 carbon atoms, COO-phenyl, COO-benzyl and -phenethyl, amino and hydroxyl, these amino and hydroxyl groups optionally being alkylated, aralkylated, acylated (preferably carboxylic acid acylated), acetalized or silylated, wherein the alkyl, acyl and acetal groups in each case contain up to 6 carbon atoms and the aralkyl group denotes benzyl or phenethyl Especially preferred compounds of the present invention are those in which R denotes a phenyl radical which is monosubstituted or disubstituted by nitro, cyano, trifluoromethyl, trifluoromethoxy, fluorine, chlorine, bromine, azido, alkoxy or alkylmercapto with in each case 1 or 2 carbon atoms, or pyridyl, $R^1$ and $R^3$ are identical or different and in each case denote a hydrogen atom or an alkyl group with 1 or 2 carbon atoms, $R^2$ denotes a hydrogen atom, an alkyl group with 1 to 4 carbon atoms or a benzyl radical, X denotes a nitrile radical, or the group of the general formula —$COOR^6$, in which $R^6$ denotes an achiral alkyl radical which has 1 to 6 carbon atoms and is optionally substituted by an alkoxy group with 1 to 4 carbon atoms, by fluorine or by an amino group, which in turn is monosubstituted by alkyl with 1 to 4 carbon atoms and carries, as the third substituent, an identical or different alkyl group with 1 to 4 carbon atoms or a benzyl radical, and $R^4$ denotes an achiral radical having, independently of $R^6$, any of the meanings given for $R^6$, the two substituents in the 3-position and 5-position always being different from one another, or $^*R^4$ represents a chiral hydrocarbon radical having a single configuration which is optionally substituted by one or two identical or different electron-attracting radicals selected from nitrile, COO-alkyl with 1 or 2 carbon atoms, COO-benzyl, amino and hydroxyl, the amino and hydroxyl groups optionally being alkylated by alkyl radicals with 1 or 2 carbon atoms, benzylated, acylated by acyl radicals with 1 to 4 carbon atoms, acetalysed by acetone or benzaldehyde or silylated by trimethylsilyl or triphenylsilyl.

The process variants (a), (b) and (c) for the production of compounds of the present invention are described in more detail, as follows.

Process variant (a)

According to process variant (a), the optically inactive racemic form of a dihydropyridine derivative of the general formula (II) is allowed to interact with a chiral substance, the diastereomeric relationships leading to resolution into the two optically active antipodes of the formula (Ia). The racemic forms of the 1,4-dihydropyridines of the formula (II) which are used as starting substances for this proccess are known or they can be prepared by known methods (see DT-OS (German Published Specification) 2,117,571 corresponding to U.S. Pat. No. 3,799,934 and DT-OS 2,508,181 corresponding to U.S. Pat. No. 4,044,141).

Examples which may be mentioned are: 5-cyano-1,4-dihydro-2,6-dimethyl-4-(2'-nitrophenyl)-pyridine-3-carboxylic acid cyclopentyl ester, 5-acetyl-1,4-dihydro-2,6-dimethyl-4-(3'-nitrophenyl)-pyridine-3-carboxylic acid isopropyl ester 5-benzoyl-1,4-dihydro-2-methyl-6-phenyl-4-(2'-trifluoromethylphenyl)-pyridine-3-carboxylic acid ethyl ester, 5-phenylsulphonyl-1,4-dihydro-2,6-dimethyl-4-(2'-chlorophenyl)-pyridine-3-carboxylic acid propyl ester, 1,4-dihydro-2,6-dimethyl-4-(3'-nitro-phenyl)-pyridine-3,5-dicarboxylic acid ethyl methyl ester, 1,4-dihydro-2,6-dimethyl-4-(2'-nitrophenyl)-pyridine-3,5-dicarboxylic acid isopropyl methyl ester, 1,4-dihydro-2,6-dimethyl-4-(2'-methoxyphenyl)-pyridine-3,5-dicarboxylic acid allyl isopropyl ester, 1,4-dihydro-2,6-dimethyl-4-(2'-cyanophenyl)-pyridine-3,5-dicarboxylic acid benzyl isopropyl ester, 1,4-dihydro-2,6-dimethyl-4-(2'-nitrophenyl)-pyridine-3,5-dicarboxylic acid isobutyl methyl ester, 1,4-dihydro-2,6-dimethyl-4-(3'-nitrophenyl)-pyridine-3,5-dicarboxylic acid isopropyl 2-methoxy-ethyl ester, 1,4-dihydro-2,6-dimethyl-4-(3'-nitrophenyl)-pyridine-3,5-dicarboxylic acid isopropyl 2-propxyethyl ester, 1,4-dihydro-2,6-dimethyl-4-(3'-nitrophenyl)-pyridine-3,5-dicarboxylic acid isopropyl 2-phenoxyethyl ester, 1,4-dihydro-2,6-dimethyl-4-(2'-chlorophenyl)-pyridine-3,5-dicarboxylic acid methyl 2,2,2-trifluoro-ethyl ester, 1,4-dihydro-2,6-dimethyl-4-(3'-nitrophenyl)-pyridine-3,5-dicarboxylic acid cyclopentyl 2,2,2-trifluoroethyl ester, 1,4-dihydro-2,6-dimethyl-4-(3'-nitrophenyl)-pyridine-3,5-dicarboxylic acid methyl 2-dimethylaminoethyl ester, 1,4-dihydro-2,6-dimethyl-4-(3'nitrophenyl)-pyridine-3,5-dicarboxylic acid methyl 2-(N-benzyl-N-methyl)-aminoethyl ester, 1,4-dihydro-2,6-dimethyl-4-(pyrid-3-yl)-pyridine-3,5-dicarboxylic acid isopropyl methyl ester, 1,4-dihydro-2,6-dimethyl-4-(pyrid-2-yl)-pyridine-3,5-dicarboxylic acid cyclopentyl 2-methoxyethyl ester, 1,4-dihydro-2,6-dimethyl-4-(2-mehylthio-pyrid-3yl)-pyridine-3,5-di-carboxylic acid ethyl methyl ester and 1,4-dihydro-2,6-dimethyl-4-(quinol-4-yl)-pyridine-3,5-dicarboxylic acid isopropyl methyl ester.

The optically active adsorbents customarily used in chromatographic separation processes may be mentioned as preferred chiral substances which can be used for this process variant (a). These adsorbents include, as preferences, variously acylated cellulose derivatives, polymeric, optically active phenylethylamine derivatives and polymeric aminoacid derivatives. Depending on the nature of the racemic compound of the general formula (II) to be resolved, it is, of course, also possible to use other optically active adsorbents, such as, optically active polysaccharides and also those optically active compounds which are firmly anchored to the surface of an inactive carrier (see: E. L. Eliel, Stereochemie der Kohlenstoffvebindungen (Stereochemistry of Carbon Compounds), Verlag Chemie (1966) and A. D. Schwanghart, W. Backmann and G. Blaschke, Chem. Ber. . 110, 778 (1977); also see the preceding for further literature).

Possible eluting agents in these preferred chromatographic separation processes are any of the inert organic solvents or mixtures thereof. These include, preferences, hydrocarbons, such as, for example, cyclohexane, petroleum ether, benzene or toluene; chlorinated hydrocarbons, such as, for example, carbon tetrachloride, chloroform or methylene chloride; ethers, such as, for example, dioxane, tetrahydrofurane or diisopropyl ether; alcohols, such as, for example, ethanol or isopropanol; or ketones and esters, such as, for example, acetone or ethyl acetate.

Process variant b

According to process variant b, the optically inactive racemic form of 1,4-dihydropyridinecarboxylic acids of the general formula (III) is reacted with an optically active base and the diastereomeric salts thereby formed are resolved into the optically active 1,4-dihydropyridinecarboxylic acids of the formula (IV), which are then esterified to give compounds of the formula (I).

The racemic 1,4-dihydropyridinecarboxylic acids of the general formula (III) used as starting substances are known (see: A. Sautin et al., Khim. Geterotsiklich Soedin, 272 (1978)), or they can be obtained in a simple manner by alkaline hydrolysis of the corresponding 1,4-dihydropyridine-3-carboxylic acid 2-cyano-ethyl esters (see: DT-OS (German Published Specification) 2,847,237).

Examples which may be mentioned are 5-cyano-1,4-dihydro-2,6-dimethyl-4-(3'-nitrophenyl)-pyridine-3-carboxylic acid, 5-acetyl-1,4dihydro-2,6-dimethyl-4-(3'-nitrophenyl)-pyridine-3-carboxylic acid, 5-benzoyl-1,4-dihydro-2-methyl-6-phenyl-4-(2'-trifluoromethylphenyl)-pyridine-3-carboxylic acid, 5-phenylsulphonyl-1,4-dihydro-2,6-dimethyl-4-(2'-chlorophenyl)-pyridine-3-carboxylic acid, 1,4-dihydro-2,6-dimetyl-4-(3'-nitrophenyl)-pyridine-3,5-dicarboxylic acid monomethyl ester, 1,4-dihydro-2,6-dimethyl-4-(2'-nitrophenyl)-pyridine-3,5-dicarboxylic acid monomethyl ester, 1,4-dihydro-2,6-dimethyl-4-(3'-nitrophenyl)-pyridine-3,5-dicarboxylic acid monoethyl ester, 1,4-dihydro-2,6-dimethyl-4-(3'-nitrophenyl)-pyridine-3,5-dicarboxylic acid monoisopropyl ester, 1,4-dihydro-2,6-dimethyl-4-(2'-nitrophenyl)-pyridine-3,5-dicarboxylic acid monoisobutyl ester, 1,4-dihydro-2,6-dimethyl-4-(3'-nitrophenyl)-pyridine-3,5-dicarboxylic acid monocyclopentyl ester, 1,4-dihydro-2,6-dimethyl-4-(2'-trifluoromethylphenyl)-pyridine-3,5-dicarboxylic acid monoethyl ester, 1,4- dihydro-2,6-dimethyl-4-(2'-cyanophenyl)-pyridine-3,5-dicarboxylic acid monobenzyl ester, 1,4-dihydro-2,6-dimethyl-4-(3'-nitrophenyl)-pyridine-3,5-dicarboxylic acid mono-(2-methoxyethyl) ester, 1,4-dihydro-2,6-dimethyl-4-(3'-nitrophenyl)-pyridine-3,5-dicarboxylic acid mono-(2'-propoxyethyl) ester, 1,4-dihydro-2,6-dimethyl-4-(2'-chlorophenyl)-pyridine-3,5-dicarboxylic acid monomethyl ester, 4dihydro-2,6-dimethyl-4-(2'-chlorophenyl)-pyridine-3,5-dicarboxylic acid mono-(2,2,2-trifluoroethyl) ester, 1,4-dihydro-2,6-dimethyl-4-(3'-nitrophenyl)-pyridine-3,5-dicarboxylic acid mono-(2-(N-benzyl-N-methylamino)-ethyl) ester, 1,4-dihydro-2,6-dimethyl-4-(2'-trifluoromethyl-phenyl)-pyridine-3,5-dicarboxylic acid monoethyl ester, 1,4-dihydro-2,6-dimethyl-4-(pyrid-2-yl)-pyridine-3,5-dicarboxylic acid monoethyl ester, 1,4dihydro-2,6-dimethyl-4-(pyrid-3-yl)-pyridine-3,5dicarboxylic acid monoethyl ester and 1,4-dihydro-2,6-dimethyl-4-(2-methylthio-pyrid-3-yl)-pyridine-3,5-dicarboxylic acid monoethyl ester.

The optically active bases used for forming the diastereomeric salts are known (see: S. H. Wilen et al., Tetrahedron 33, 2725 (1977)).

Examples which may be mentioned are: cinchonine, cinchonidine, quinine, quindine, brucine, strychnine, morphine, ephedrine, α-phenylethylamine, α-(2-naphthyl)-ethylamine, menthylamine, amphetamine and dehydroabietylamine.

When the racemic 1,4-dihydropyridinecarboxylic acids of the formula (III) are reacted with one of the abovementioned optically active bases, diastereomeric salts are formed. These differ from one another in respect of their physical properties and can thus be separated from one another with the aid of known methods. Preferred separation processes which may be mentioned are recrystallisation from a suitable inert solvent, separation by thin layer chromatography or column chromatography or separation by high performance liquid chromatography.

The diastereomeric salts which are separated with the aid of these methods and have a single configuration are converted into optically active 1,4-dihydropyridinecarboxylic acids of the formula (IV) by adding inorganic or lower organic acids, for example, hydrochloric acid or hydrobromic acid, dilute sulphuric or phosphoric acid or acetic acid, or with the aid of ion exchangers.

The optically active acids of the formula (IV), thus obtained are preferably converted into the correspond optically active esters of the formula (I) by esterification by known methods, for example via the corresponding carboxlyic acid azolides or by the dicyclohexylcarbodiimide method (see H. A. Staab and W. Rohr, Neuere Methoden der präparativen organischen Chemie (Recent Methods of Preparative Organic Chemistry), Volume V, page 53 et seq. (1967) and B. Neires and W. Steglich, Angew. Chem. 90, 556 (1978)).

Process variant (c)

Accorddding to variant c, a dihydropyridine ester of the formula (VI) which has an optically active alcohol component (—*OR$^8$) is first synthesised by a customary 1,4-dihydropyridine synthesis. Because of the two possible, opposite configurations on the C$_4$ atom of the 1,4-dihydropyridine ring, 2 diastereomers are thereby formed. These are separated by customary methods and the optically active alcohol component is then optionally replaced by an achiral, optically inactive alcohol component (—OR$^4$), so that compounds of the formula (Ia) are formed. The optically active alcohol component —*OR$^8$ is optionally replaced by a correspondingly chiral, optically active alcohol component —*OR$^4$, so that compounds of the formula (Ib) are formed.

Bothe dextro-rotatory and laevo-rotatory alcohol radicals can be used as the alcohol components —*OR$^8$ in the formula (VI) in process variant c), so that the configuration of the radical —*OR$^8$ need not be specified in more detail in the following text.

The diastereomeric 1,4-dihydropyridine derivatives of the formula (VI) used as starting substances in process variang (c) are known (see DT-OS (German Published Specification) 2,117,571), or they can be prepared by known methods by reacting corresponding ylidenes with β-aminocrotonic acid esters, the ester radical of which carries an optically active alcohol component.

Examples which may be mentioned are: 5-cyano-1,4-dihydro-2,6-dimethyl-4-(3'-nitrophenyl)-pyridine-3-carboxylic acid α-cyanoethyl ester, 5-acetyl-1,4-dihydro-2,6-dimethyl-4-(3'-nitrophenyl)-pyridine-3-carboxylic acid α-cyanoethyl ester, 5-benzoyl-1,4-dihydro-2-methyl-6-phenyl-4-(2'-trifluoromethyl)-pyridine-3-carboxylic acid α-cyanoethyl ester, 5-phenylsulphonyl-1,4-dihydro-2,6-dimethyl-4-(2'-chlorophenyl)-pyridine-3-carboxylic acid α-methoxycarbonylethyl ester, 1,4-dihydro-2,6-dimethyl-4-(3'-nitrophenyl)-pyridine-3,5-dicarboxylic acid methyl α-cyanoethyl ester, 1,4-dihydro-2,6-dimethyl-4-(3'-nitrophenyl)-pyridine-3,5-dicarboxylic acid methyl α-methoxycarbonylethyl ester, 1,4-dihydro-2,6-dimethyl-4-(3'-nitrophenyl)-pyridine-3,5-dicarboxylic acid methyl α-methoxycarbonylbenzyl ester, 1,4-dihydro-2,6-dimethyl-4-(3'-nitrophenyl)-pyridine-3,5-dicarboxylic acid methyl β-methoxy-β-phenyl-ethyl ester, 1,4-dihydro-2,6-dimethyl-4-(3'-nitrophenyl)-pyridine-3,5-dicarboxylic acid ethyl α-cyanoethyl ester, 1,4-dihydro-2,6-dimethyl-4-(3'-nitrophenyl)-pyridine-3,5-dicarboxylic acid ethyl α-methoxycarbonylbenzyl ester, 1,4-dihydro-2,6-dimethyl-4-(2'-nitrophenyl)-pyridine-3,5-dicarboxylic acid ethyl β-methoxy-β-phenyl-ethyl ester, 1,4-dihydro-2,6-dimethyl-4-(3'-nitrophenyl)-pyridine-3,5-dicarboxylic acid methyl 2,2-dimethyl-1,3-dioxolan-4-yl-methyl ester, 1,4-dihydro-2,6-dimethyl-4-(3'-nitrophenyl)-pyridine-3,5-dicarboxylic acid ethyl 2,2-dimethyl-1,3-dioxolan-4-yl-methyl ester, 1,4-dihydro-2,6-dimetyl-4-(3'-nitrophenyl)-pyridine-3,5-dicarboxylic acid isopropyl α-cyanoethyl ester, 1,4-dihydro-2,6dimethyl-4-(3'-nitrophenyl)-pyridine-3,5-dicarboxylic acid isopropyl α-cyanobenzyl ester, 1,4-dihydro-2,6-dimethyl-4-(3'-nitrophenyl)-pyridine-3,5-dicarboxylic acid isopropyl α-methoxycarbonylethyl ester, 1,4-dihydro-2,6-dimethyl-4-(3'-nitrophenyl)-pyridine-3,5-dicarboxylic acid isopropyl α-methoxycarbonylbenzyl ester, 1,4-dihydro-2,6-dimethyl-4-(3'-nitrophenyl)-pyridine-3,5-dicarboxylic acid isopropyl β-methoxy-β-phenylethyl ester, 1,4-dihydro-2,6-dimethyl-4-(3'-nitrophenyl)-pyridine-3,5-dicarboxylic acid isopropyl 2,2-dimethyl-1,3-dioxolan-4-yl-methyl ester, 2-[1,4-dihydro-5-(2-propoxycarbonyl)-2,6-dimethyl-4-(3'-nitrophenyl)-3-pyridylcarbonyloxy]-ethyl β-D-glucopyranoside, 2-[1,4-dihydro-5-methoxycarbonyl-2,6-dimethyl-4-(2'-chlorophenyl)-3-pyridylcarbonyloxy]-ethyl β-D-glucopyranoside, 1,4-dihydro-2,6-dimethyl-4-(2'-chlorophenyl)-pyridine-3,5-dicarboxylic acid methyl α-cyanoethyl ester, 1,4-dihydro-2,6-dimethyl-4-(2'-nitrophenyl)-pyridine-3,5-dicarboxylic acid isobutyl β-methoxy-β-phenyl-eth 1 ester, 1,4-dihydro-2,6-dimethyl-4-(2'-chlorophenyl)-pyridine-3,5-dicarboxylic acid methyl α-methoxycarbonylethyl ester, 1,4-dihydro-2,6-dimethyl-4-(2'-chlorophenyl)- pyridine-3,5-dicarboxylic acid methyl β-methoxy-β-phenyl-ethyl ester, 1,4-dihydro-2,6-dimethyl-4-(pyrid-2-yl)-pyridine-3,5-dicarboxylic acid methyl β-methoxy-β-phenyl-ethyl ester and 1,4-dihydro-2,6-dimethyl-4-(pyrid-3-yl)-pyridine-3,5-dicarboxylic acid ethyl β-methoxy-β-phenyl-ethyl ester.

As diastereomers, the compounds of the formula (VI) formed according to variant (c) differ from one another in respect of their physical and chemical properties and can thus be separated from one another with the aid of known methods. Preferred separation methods which may be mentioned are: recrystallisation from inert solvents, thin layer chromatography, column chromatography and high performance liquid chromatography.

The separated 1,4-dihydropyridine derivatives of the formula (VII) having a single configuration are moreover suitable as intermediate products for the simple preparation of compounds of the formula (Ia) and (Ib) and, in the case where *R$^8$ has the meaning of *R$^4$, are already valuable pharmacological active compounds. The trans-esterification of the compounds (VII) which may be required is preferably carried out by alkaline alkanolysis, if appropriate in the presence of an inert additional solvent, using R$^4$—O$^\ominus$ or *R$^4$—O$^\ominus$ as the alcoholic agent, R$^4$ and *R$^4$ having the meaning indicated above.

Possible solvents for this trans-esterification are any of the inert organic solvents or mixtures thereof. These include, as preferences, ethers, such as dioxane, tetrahydrofurane, glycol monomethyl ether or glycol dimethyl ether, or dimethylformamide, dimethylsulphoxide, acetonitrile, pyridine or hexamethylphosphoric acid triamide.

The reaction temperatures can be varied within a substantial range. In general, the reaction is carried out between 20° and 150° C., preferably at about 50° to 100° C.

The reaction can be carried out under normal pressure, but also under increased pressure. In general, it is carried out under normal pressure.

Preferred alcoholysis agents are alkali metal alcoholates, such as sodium alcoholates or potassium alcoholates. There are in each case employed in molar amounts or in a slight excess in carrying out the alcoholysis.

A further possibility for the last step for process variant (c), as mentioned, consists in first hydrolysing the 1,4-dihydropridine derivatives of the formula (VII) having a single configuration to give the optically active 1,4-dihydropyridinecarboxylic acids of the formula (IV) having a single configuration, and then esterifying these acids (as described under process variant b) to give the compounds of the formula (Ia) and (Ib) according to the invention.

Preferred possible hydrolysis agents for this hydrolysis are inorganic bases. These include, in particular, alkali metal hydroxides, such as sodium hydroxide or potassium hydroxide. The bases can be employed in molar amounts or in a 2- to 3-fold excess, depending on the nature of the organic starting compound.

A large excess of water has proved an advantageous reaction medium. In order to carry out the reaction in a homogeneous system, it is as a rule appropriate to add an inert, water-miscible organic solvent. These solvents include, preferably, alcohols, such as methanol, ethanol or propanol, ethers, such as dioxane, tetrahydrofurane or 1,2-dimethoxyethane, or pyridine, dimethylformamide, dimethylsulphoxide or hexamethylphosphoric acid triamide.

In addition to the preparation examples listed below, the following optically active compounds according to the invention may be mentioned: 1,4-dihydro-2,6-dimethyl-4-(3'-nitrophenyl)-pryridine-3,5-dicarboxylic acid methyl ethyl ester, 1,4-dihydro-2,6-dimethyl-4-(3'-nitrophenyl)-pyridine-3,5-dicarboxylic acid methyl propyl ester, 1,4-dihydro-2,6-dimethyl-4-(3'-nitrophenyl)-pyridine-3,5-dicarboxylic acid methyl cyclopentyl ester, 1,4-dihydro-2,6-dimethyl-4-(3'-nitrophenyl)-pyridine-3,5-dicarboxylic acid methyl 2-methoxy-ethyl ester, 1,4-dihydro-2,6-dimethyl-4-(3'-nitrophenyl)-pyridine-3,5-dicarboxylic acid methyl benzyl ester, 1,4-dihydro-2,6-dimethyl-4-(3'-nitrophenyl)-pyridine-3,5-dicarboxylic acid methyl 2-phenoxyethyl ester, 1,4-dihydro-2,6-dimethyl-4-(3'-nitrophenyl)-pyridine-3,5-dicarboxylic acid methyl 2-dimethylaminoethyl ester, 1,4-dihydro-2,6-dimethyl-4-(3'-nitrophenyl)-pyridine-3,5-dicarboxylic acid methyl 2-N-benzyl-N-methylaminoethyl ester, 1,4-dihydro-2,6-dimethyl-4-(2'-nitrophenyl)-pyridine-3,5-dicarboxylic acid methyl ethyl ester, 1,4-dihydro-2,6-dimethyl-4-(2'-nitrophenyl)-pyridine-3,5-dicarboxylic acid methyl isopropyl ester, 1,4-dihydro-2,6-dimethyl-4-(2'-nitrophenyl)-pyridine-3,5-dicarboxylic acid methyl cyclopentyl ester, 1,4-dihydro-2,6-dimethyl-4-(2'-nitrophenyl)-pyridine-3,5-dicarboxylic acid methyl isobutyl ester, 1,4-dihydro-2,6-dimethyl-4-(2'-nitrophenyl)-pyridine-3,5-dicarboxylic acid methyl benzyl ester, 1,4-dihydro-2,6-dimethyl-4-(3'-nitrophenyl)-pyridine-3,5-dicarboxylic acid methyl 3-phenoxypropyl ester, 1,4-dihydro-2,6-dimethyl-4-(2'-nitrophenyl)-pyridine-3,5-dicarboxylic acid ethyl isobutyl ester, 1,4-dihydro-2,6-dimethyl-4-(2'-chlorophenyl)-pyridine-3,5-dicarboxylic acid methyl 2,2,2-trifluoroethyl ester, 1,4-dihydro-2,6-dimethyl-4-(2'-chlorophenyl)-pyridine-3,5-dicarboxylic acid ethyl 2,2,2-trifluoroethyl ester, 1,4-dihydro-2,6-dimethyl-4-(3'-nitrophenyl)-pyridine-3,5-dicarboxylic acid isopropyl 2-propoxyethyl ester, 1,4-dihydro-2,6-dimethyl-4-(3'-nitrophenyl)-pyridine-3,5-dicarboxylic acid isopropyl 2-phenoxyethyl ester, 1,4-dihydro-2,6-dimethyl-4-(3'-nitrophenyl)-pyridine-3,5-dicarboxylic acid isopropyl 2-N-benzyl-N-methylaminoethyl ester, 1,4-dihydro-2,6-dimethyl-4-(3'-nitrophenyl)-pyridine-3,5-dicarboxylic acid isopropyl 2-dimethylaminoethyl ester, 1,4-dihydro-2,6-dimethyl-4-(2'-trifluoromethylphenyl)-pyridine-3,5-dicarboxylic acid isopropyl methyl ester, 1,4-dihydro-2,6-dimethyl-4-(2'-trifluoromethylphenyl)-pyridine-3,5-dicarboxylic acid ethyl isopropyl ester, 1,4-dihydro-2,6-dimethyl-4-(pyrid-3-yl)-pyridine-3,5-dicarboxylic acid ethyl methyl ester, 1,4-dihydro-2,6-dimethyl-4-(pyrid-3-yl)-pyridine-3,5-dicarboxylic acid isopropyl methyl ester, 1,4-dihydro-2,6-dimethyl-4-(pyrid-2-yl)-pyridine-3,5-dicarboxylic acid isopropyl methyl ester 1,4-dihydro-2,6-dimethyl-4-(2-chloropyrid-3-yl)-pyridine-3,5-dicarboxylic acid ethyl methyl ester, 1,4-dihydro-2,6-dimethyl-4-(2-chloropyrid-3-yl)-pyridine-3,5-dicarboxylic acid ethyl isopropyl ester, 1,4-dihydro-2,6-dimethyl-4-(2-methyl-pyrid-3-yl)-pyridine-3,5-dicarboxylic acid ethyl methyl ester and 1,4-dihydro-2,6-dimethyl-4-(2-methylthiophenyl-3)-pyridine-3,5-dicarboxylic acid isopropyl methyl ester. These compounds can be preferably prepared according to the process (C) analogously to examples 1 and 2.

The compounds according to the invention can be used as medicaments, in particular as active compounds having an influence on vessels and circulation. They have a broad and diverse pharmacological action spectrum. In detail, the following main actions could be demonstrated in animals experiments:

1. The compounds produce a distinct and long-lasting dilation of the coronary vessels on parenteral, oral and perlingual administration. This action on the coronary vessels is intensified by a simultaneous nitrite-like effect of reducing the load on the heart.

They influence or modify heart metabolism in the sense of a saving of energy.

2. The excitability of the stimulus formation and excitation conduction system within the heart is lowered, so that an antifibrillation action which can be demonstrated at therapeutic doses, results.

3. The tone of the smooth muscle of the vessels is greatly reduced under the action of the compounds. This vascular-spasmolytic action can take place in the entire vascular system or can manifest itself more or less isolated in circumscribed vascular regions, such as, for example, the central nervous system, in particular in the cerebral region.

4. The compounds lower the blood pressure of hypertonic animals and can thus be used as antihypertensive agents.

5. The compounds have a powerful muscular-spasmolytic action which manifests itself on the smooth muscle of the stomach, intestinal tract, urogenital tract and respiratory system.

On the basis of these properties, the compounds according to the invention are particularly suitable for the prophylaxis and therapy of acute and chronic ischaemic heart disease in the broadest sense, for the therapy of hypertension and for the treatment of disorders in cerebral and peripheral blood flow.

As stated above, the invention also relates to the use in medicine of the compounds of the invention.

The present invention provides a pharmaceutical composition containing as active ingredient a compound of the invention in admixture with a solid or liquefied gaseous diluent, or in admixture with an inert pharmaceutical carrier, such as a liquid diluent other than a solvent of a molecular weight less than 200 (preferably less than 350) expect in the presence of a surface active agent.

The invention further provides a pharmaceutical composition containing as active ingredient a compound of the invention in the form of a sterile and/or physiologically isotonic aqueous solution.

The invention also provides a medicament in dosage unit form comprising a compound of the invention.

The invention also provides a medicament in the form of tablets (including lozenges and granules), dragees, capsules, pills, ampoules or suppositories comprising a compound of the invention.

"Medicament" as used in this Specification means physically discrete coherent portions suitable for medical administration. "Medicament in dosage unit form" as used in this Specification means physically discrete coherent units suitable for medical administration each containing a daily dose or a multiple (up to four times) or submultiple (down to a fortieth) of a daily dose of the compound of the invention in association with a carrier and/or enclosed within an envelope. Whether the medicament contains a daily dose or, for example, a half, a third or a quarter of a daily dose will depend on whether the medicament is to be administered once or, for example, twice, three times or four times a day respectively.

The pharmaceutical composition according to the invention may, for example, take the form of suspensions, solutions and emulsions of the active ingredient in aqueous or non-aqueous diluents, syrups, granulates or powders.

The diluents to be used in pharmaceutical compositions (e.g. granulates) adapted to be formed into tablets, dragees, capsules and pills include the following: (a) fillers and extenders, e.g. starch, sugars, mannitol, and silicic acid; (b) binding agents, e.g. carboxymethyl cellulose and other cellulose derivatives, alginates, gelatine and polyvinyl pyrrolidone; (c) moisturizing agents, e.g. glycerol; (d) disintegrating agents, e.g. agar-agar, calcium carbonate and sodium bicarbonate; (e) agents for retarding dissolution e.g. paraffin; (f) resorption accelerators, e.g. quaternary ammonium compounds; (g) surface active agents, e.g. cetyl alcohol, glycerol monostearate; (h) adsorptive carriers, e.g. kaolin and bentonite; (i) lubricants, e.g. talc, calcium and magnesium stearate and solid polyethyl glycols.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, of polymeric substances or waxes.

The ingredient can also be made up in microencapsulated form together with one or several of the above-mentioned diluents.

The diluents to be used in pharmaceutical compositions adapted to be formed into suppositories can, for example, be the usual water-soluable diluents, such as polyethylene glycols and fats (e.g. cocoa oil and high esters (e.g. $C_{14}$-alcohol with $C_{16}$-fatty acid)) or mixtures of these diluents.

The pharmaceutical compositions which are solutions and emulsions can, for example, contain the customary diluents (with, of course, the above-mentioned exclusion of solvents having a molecular weight below 200 except in the presence of a surface-active agent), such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils (for example ground nut oil), glycerol, tetrahydrofurfuryl alcohol, polyethylene glycols and fatty acid esters of sorbitol or mixtures thereof.

For parenteral administration, solutions and emulsions should be sterile, and, if appropriate, blood-isotonic.

The pharmaceutical compositions which are suspensions can contain the usual diluents, such as liquid diluents, e.g. water, ethyl alcohol, propylene glycol, surface-active agents (e.g. ethoxylated isostearyl alcohols, polyoxyethylene sorbite and sorbitane esters), microcrystalline cellulose, aluminium metahydroxide, bentonite, agar-agar and tragacanth or mixtures thereof.

All the pharmaceutical compositions according to the invention can also contain colouring agents and preservatives as well as perfumes and flavouring additions (e.g. peppermint oil and eucalyptus oil) and sweetening agents (e.g. saccharin).

The pharmaceutical compositions according to the invention generally contain from 0.5% to 90% of the active ingredient by weight of the total composition.

In addition to a compound of the invention, the pharmaceutical compositions and medicaments according to the invention can also contain other pharmaceutically active compounds. They may also contain a plurality of compounds of the invention.

Any diluent in the medicaments of the present invention may be any of those mentioned above in relation to the pharmaceutical compositions of the present invention. Such medicaments may include solvents of molecular weight less than 200 as sole diluent.

The discrete coherent portions constituting the medicament according to the invention will generally be adapted by virtue of their shape or packaging for medical administration and may be, for example, any of the following: tablets (including lozenges and granulates), pills, dragees, capsules, suppositories and ampoules. Some of these forms may be made up for delayed release of the active ingredient. Some, such as capsules, include a protective envelope which renders the portions of the medicament physically discrete and coherent.

The preferred daily dose for administration of the medicaments of the invention is 2.5 mg to 50 mg in the case of intravenous administration, and 5 mg to 250 mg in the case of oral administration of active ingredient.

The production of the above-mentioned pharmaceutical compositions and medicaments is carried out by any method known in the art, for example, by mixing the active ingredient (s) with the diluent (s) to form a pharmaceutical composition (e.g. a granulate) and then forming the composition into the medicament (e.g. tablets).

This invention further provides a method of combating the above-mentioned diseases in warm-blooded animals, which comprises administering to the animals a compound of the invention alone or in admixture with a diluent or in the form of a medicament according to the invention.

It is envisaged that these active compounds will be administered perorally, parenterally (for example intramuscularly, intraperitoneally, subcutaneously and intravenously), or rectally, preferably orally or parenterally, especially perlingually or intravenously. Preferred pharmaceutical compositions and medicaments are therefore those adapted for administration such as oral or parenteral administration. Administration in the method of the invention is preferably oral or parenteral administration.

In general it has proved advantageous to administer amounts of from 0.001 mg to 10 mg/kg, preferably 0.05 mg to 1 mg/kg of body weight per day in the case of intravenous administration and 0.05 mg to 20 mg, preferably 0.1 to 5 mg/kg of body weight per day in the case of oral administration, to achieve effective results. Nevertheless, it can at times be necessary to deviate from those dosage rates, and in particular to do so as a function of the nature and body weight of the human or animal subject to be treated, the individual reaction of this subject to the treatment, the type of formulation in which the active ingredient is administered and the mode in which the administration is carried out, and the point in the progress of the disease or interval at which it is to be administered. Thus it may in some case suffice to use less than the above-mentioned minimum dosage rate, whilst other cases the upper limit mentioned must be exceeded to achieve the desired results. Where larger amounts are administered it can be advisable to divide these into several individual administrations over the course of the day.

The optical purity of the compounds of the formulae (Ia) and (Ib) obtained by the following preparation examples and of the particular starting materials and intermediate products was examined and confirmed by proton resonance spectroscopy, by addition of (chiral) lanthanide shift agents.

The following Preparative Examples illustrate the preparation of compounds of the present invention.

Preparative Examples (according to process variant (c))

(A) Preparation of (+)-1,4-dihydro-2,6-dimethyl-4-(3'-nitrophenyl)-pyridine-3,5-dicarboxylic acid isopropyl 2-methoxy-2-phenylethyl ester (compound A)

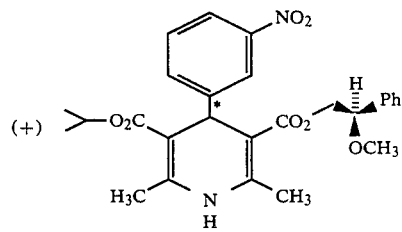

A solution of 14.5 g (96 mmols) of 3-nitrobenzaldehyde, 13.7 g (96 mmols) of β-aminocrotonic acid isopropyl ester and 22.8 g (96 mmols) of acetoacetic acid 2-methoxy-2-phenylethyl ester in 150 ml of isopropanol is heated to the boiling point under nitrogen for 12 hours.

The solvent is then distilled off in vacuo and the oily residue is triturated with a little ether, whereupon the reaction product partly solidified. The crystals which has precipitated was filtered off and recrystallised from ethanol. Melting point: m.p. = 173° C., yield: 19 g (40%)

This crystalline fraction is a single configuration and the specific optical rotation $[\alpha]_D^{20} = +53.82°$ (c=1,1% w/v*, ethanol)

* w/v = weight per volume (B) Preparation of (-)-1,4-dihydro-2,6-dimethyl-4-(3'-nitrophenyl)-pyridine-3,5-dicarboxylic acid isopropyl 2-methoxy-2-phenylethyl ester (compound (b)

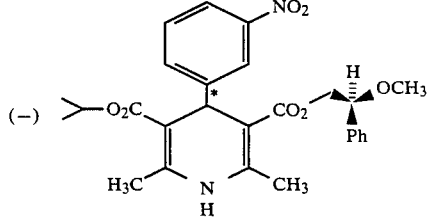

A solution of 27.7 g (0.1 mol) of 3'-nitrobenzylideneacetoacetic acid isopropyl ester and 23.5 g (0.1 mol) of β-aminocrotonic acid 2-methoxy-2-phenylethyl ester in 160 ml of methanol is heated to the boiling point under nitrogen for 12 hours. The solvent is then distilled off in vacuo and the oily residue is triturated with a little ether. The reaction product thereby solidified and is filtered off and recrystallised from ethanol.

Melting point: m.p. = 173° C., yield: 11.8 (24%)

The product has a single configuration and the specific optical rotation $[\alpha]_D^{20} = -53.3°$ (c=1.04% w/v, ethanol).

Example 1

(+)-1,4-Dihydro-2,6-dimethyl-4-(3'-nitrophenyl)-pyridine-3,5-dicarboxylic acid isopropyl methyl ester

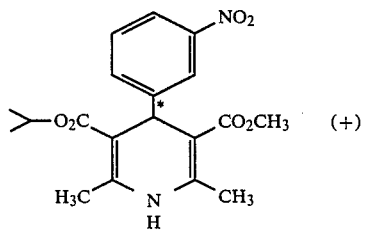

19 g (38 mmols) of (+)-1,4-dihydro-2,6-dimethyl-4-(3'-nitrophenyl)-pyridine-3,5-dicarboxylic acid isopropyl 2-methoxy-2-phenylethyl ester (compound A) in a solution of 0.87 g (38 mmols) of sodium in 50 ml of methanol and 50 ml of 1,2-dimethoxyethane are heated to the boiling point under nitrogen for 5 hours. The solution is then concentrated to half the volume in vacuo and acidified with dilute hydrochloric acid. After adding an equal part of water, the mixture is extracted several times with methylene chloride and the extracts are concentrated in vacuo, after drying over sodium sulphate. The solid residue is recrystallized from methanol (crude yield: 5.5 g (3.%), melting point: 134°–136° C.) and the product is then purified by high performance liquid chromatography on a preparative RP8 column (10μ), internal diameter 16 mm, length 250 mm, using acetonitrile/water =45/55 as the eluting agent.

Melting point: m.p. =136° C.

Specific optical rotation: $[\alpha]_D^{20} = +24.97$ (c=0.93% w/v, ethanol).

Example 2

(−)-1,4-Dihydro-2,6-dimethyl-4-(3'-nitrophenyl)-pyridine-3,5-dicarboxylic acid isopropyl methyl ester

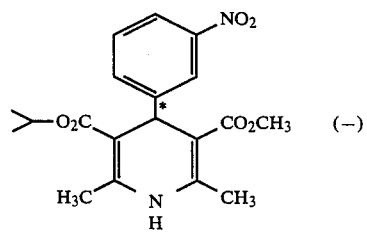

16.5 g (33.4 mmols) of (−)-1,4-dihydro-2,6-dimethyl-4-(3'-nitrophenyl)-pyridine-3,5-dicarboxylic acid isopropyl 2-methoxy-2-phenylethyl ester (compound B) in a solution of 0.87 g (38 mmols) of sodium in 100 ml of methanol are heated to the boiling point under nitrogen for 24 hours. After cooling, the solution is concentrated to about half the volume in vacuo and acidified with dilute hydrochloric acid. After adding an equal part of water, the mixture is extracted several times with methylene chloride and the extracts are concentrated in vacuo, after drying over sodium sulphate. The residue crystallized completely and is filtered off and recrystallized from methanol (crude yield: 4.2 g (34%), melting point: 132°–134° C.), and the product is purified by high performance liquid chromatography, as described under Example 1.

Melting point: m.p. =136° C.

Specific optical rotation: $[60]_D^{20} = -24.60°$ (c =1.07% w/v, ethanol).

Example 3

(+)-1,4-Dihydro-2,6-dimethyl-4-(3'-nitrophenyl)-pyridine-3,5-dicarboxylic acid ethyl isopropyl ester

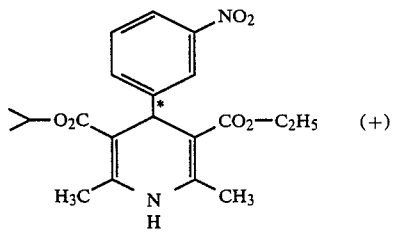

19 g (38 mmols) of (+)-1,4-dihydro-2,6-dimethyl-4-(3'-nitrophenyl)-pyridine-3,5-carboxylic acid isopropyl 2-methoxy-2-phenylethyl ester (compound A) in a solution of 0.87 g (38 mmols) of sodium in 100 ml of ethanol are heated to the boiling point under nitrogen for 8 hours. The solvent is then distilled off in vacuo, the residue is taken up in water and the mixture is acidified with dilute hydrochloric acid and extracted several times with methylene chloride. The extracts are concentrated in vacuo, after drying over sodium sulphate. The residue crystallised completely and is filtered off and recrystallised from methanol (crude yield: 4.1 g (2,%), melting point: 143°–146° C.), and the product is purified by high performance liquid chromatography, as described under Example 1.

Melting point: m.p. =140° C.

Specific optical rotation: $[\alpha]_D^{20} = +4.61$ (c =0.46% w/v, ethanol).

Example 4

(−)-1,4-Dihydro-2,6-dimethyl-4-(3'-nitrophenyl)-pyridine-3,5-dicarboxylic acid ethyl isopropyl

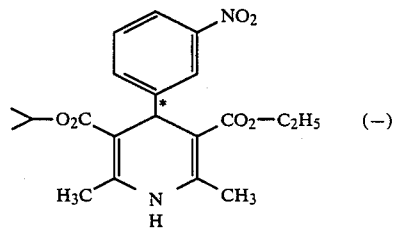

18.6 g (27.6 mmols) of (−)-1,4-dihydro-2,6-dimethyl-4-(3'-nitrophenyl)-pyridine-3,5-dicarboxylic acid isopropyl 2-methoxy-2-phenylethyl ester (compound (B) in a solution of 0.86 g (3m.6 mmols) of sodium in 100 ml of ethanol are heated to the boiling point under nitrogen for 8 hours. The solution is then concentrated to about half the volume in vacuo, acidified with dilute hydrochloric acid and, after adding an equal part of water, extracted several times with methylene chloride. The extracts are concentrated in vacuo, after drying over sodium sulphate. The residue initially obtained as an oil soon crystallized completely and is filtered off and recrystallised from methanol (crude yield: 2.8 g (19,2%), melting point: 146°–149° C.), and the product is purified by high performance liquid chromatography, as described under Example 1.

Melting point: m.p. = 140°
Specific optical rotation: $[\alpha]_D^{20} = -4.75$ (c = 0.51% w/v, ethanol).

Example 5

(+)-1,4-Dihydro-2,6-dimethyl-4-(3'-nitrophenyl)-pyridine-3,5-dicarboxylic acid isopropyl 2-methoxyethyl ester

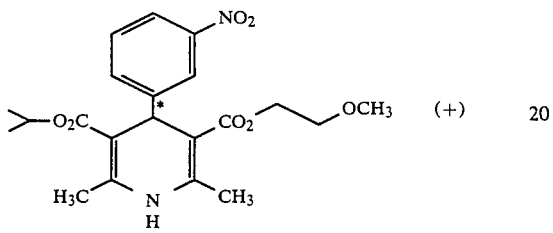

24.7 g (50 mmols) of (+)-1,4-dihydro-2,6-dimethyl-4-(3'-nitrophenyl)-pyridine-3,5-dicarboxylic acid isopropyl-2-methoxy-2-phenylethyl ester (compound A) are stirred in a solution of 1.4 g (61 mmols) of sodium in 230 ml of freshly distilled glycol monomethyl ether at 85° C. under nitrogen for 8 hours. After cooling, the solvent is distilled off in vacuo, the residue is taken up in water and the mixture is acidified with dilute hydrochloric acid and extracted several times with methylene chloride. The organic extracts are concentrated, after drying over sodium sulphate, and the oily residue is triturated with a little ether, where-upon the substance rapidly crystallizes completely. The solid reaction product is filtered off (crude
yield: 15.1 g (72%),
melting point: 126°–129° C.) and recrystallized twice from ethanol.
Melting point: m.p. = 134° C.
Specific optical rotation: $[\alpha]_D^{20} = +17.10°$ (c = =0.96% w/v, ethanol).

Example 6

(−)-1,4-dihydro-2,6-dimethyl-4-(3'-nitrophenyl)-pyridine-3,5-dicarboxylic acid isopropyl 2-methoxyethyl ester

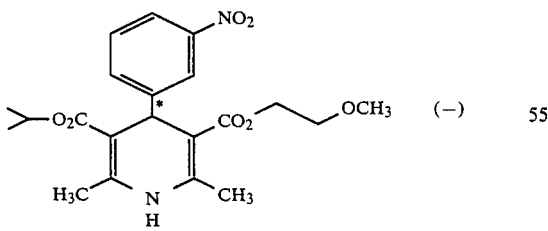

8.2 g (16.6 mmols) of (−)-1,4-dihydro-2,6-dimethyl-4-(3'-nitrophenyl)-pyridine-3,5-dicarboxylic acid isopropyl-2-methoxy-2-phenylethyl ester (compound B) are stirred in a solution of 0.5 g (21.8 mmols) of sodium in 80 ml of freshly distilled gylcol monomethyl ether at 85° C. under nitrogen for 8 hours. After cooling, the solvent is distilled off in vacuo, the residue is taken up in water and the mixture is acidified with dilute hydrochloric acid and extracted several times with methylene chloride. The organic extracts are concentrated, after drying over sodium sulphate. The oily residue soon crystallizes completely and, after adding a little ether, is filtered off (crude yield: 5.1 g (73%)) and recrystallized twice from ethanol.
Melting point: m.p. = 134° C.
Specific optical rotation: $[\alpha]_D^{20} = -16.9$ (c = 1.5% w/v, ethanol).

Example 7

(−)-1,4dihydro-2,6-dimethyl-4-(3-nitrophenyl)-pyridine-3,5-dicarboxylic acid ethyl methyl ester

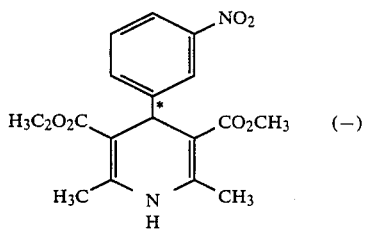

7,5 g (16 mmoles) of (−)-1,4-Dihydro-2,6-dimethyl-4-(3-nitrophenyl)-pyridine-3,5-dicarboxylic acid ethyl 2-(S)-methoxy-2-phenylethyl) ester (compound B) in a solution of 0,41 g (18 mmoles) of sodium in 75 ml of methanol heated to the boiling point under nitrogen for 5 hours. The solvent is then distilled off in vacuo, the residue is taken up in water and the mixture is acidified with dilute hydrochloride acid and extracted several times with methylene chloride. The organic extracts are concentrated in vacuo, after drying over sodium sulphate. The only residue crystallised completely (crude yield: 3,5 g) and the product is then purified by higher performance liquid chromatography as described in example 1.
Melting point: m.p. = 159°–160° C.
Specific optical rotation $[\alpha]_D^{20} = -15.02°$ C. (c = 0,49 w/v, ethanol).

Example 8

(+)-1,4-Dihydro-2,6-dimethyl-4-(3'-nitrophenyl)pyridine-3,5-dicarboxylic acid isobutyl methyl ester

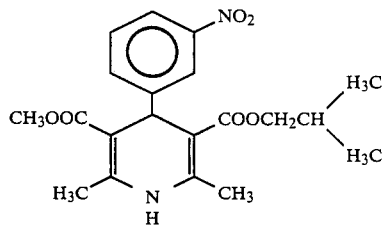

is obtained analogeously to the method described in example 7 by selective alcoholyse of the compond of the formula D by using isobutanole.
Melting point: m.p. = 138° C.
Specific optical rotation: $[\alpha]_D^{20} = +25,9°$ C. (c=0.50 ethanol)

Example 9

The compound (+)-1,4-Dihydro-2,6-dimethyl-4-(3'-nitrophenyl)-pyridine-3,5-dicarboxylic acid methyl neopentyl ester of the formula

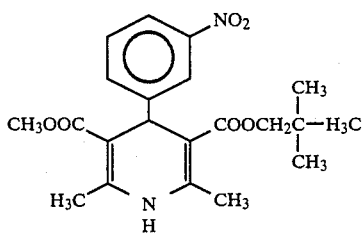

is obtained analogeously to the method described in example 7 by selective alcoholyse of the compound of the formula D with neopentyl alcohol.

Melting point: m.p. = 131° C.

Specific optical rotation: $[\alpha]^{D20} = +53.4°$ (c=0,51 ethanol

Example 10

The compound (=)-1,4-Dihydro-2,6-dimethyl-4-(2'-nitriphenyl)-pyridine-3,5-dicarboxylic acid isobutyl methyl ester of the formula

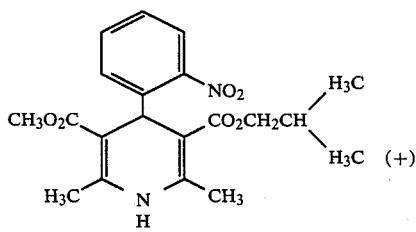

is obtained as a yellowish oil which builds an amorpheous product after drying in vacuo. Specific optical rotation: $[\alpha]_D^{20} = +165.93°$ C. (c=0,512, ethanol).

Among the new optically active 1,4-dihydro-pyridine salts of the invention, those salts that are pharmaceutically acceptable are particularly important and are preferred.

The new free optically active 1,4-dihydro-pyridine compounds of the general formula (Ia) and their salts can be interconverted in any suitable manner; methods for such interconversion are known in the art.

The present invention also comprises pharmaceutically acceptable bioprecursors of the active compounds of the present invention.

For the purpose of this specification the term pharmaceutically acceptable bioprecursor' of an active compound of the invention means a compound having a structural formula different from the active compound but which nonetheless, upon administration to a warmblooded animal is converted in the patient's body to the active compound.

What is claimed is:

1. The compound (+)-1,4-dihydro-2,6-dimethyl-4-(2'-nitrophenyl)-pyridine-3,5-dicarboxylic acid methyl isobutyl ester.

2. A pharmaceutical composition comprising, as an active ingredient, a coronary dilator effective amount of a compound according to claim 1 in admixture with an inert pharmaceutical carrier.

3. A pharmaceutical composition of claim 2 in the form of a sterile or physiologically isotonic aqueous solution.

4. A composition according to claim 2 or 3 containing from 0.5 to 90% by weight of the said active ingredient.

5. A medicament in dosage unit form comprising an amount of a compound according to claim 1 as a coronary dilator together with an inert pharmaceutical carrier.

6. A medicament of claim 5 in the form of tablets, pills, dragees, capsules, ampoules or suppositories.

7. A method of effecting coronary dilation in warm-blooded animals which comprises administering to the animals a coronary dilation influencing amount of an active compound according to claim 1 either alone or in admixture with an inert pharmaceutical carrier or in the form of a medicament.

8. A method according to claim 7 in which the active compound is administered intravenously in an amount of 0.05 to 1 mg per kg body weight per day.

9. A method according to claim 7 in which the active compound is administered orally in an amount of 0.1 to 5 mg per kg body weight per day.

* * * * *